(12) United States Patent
Morris et al.

(10) Patent No.: US 6,321,123 B1
(45) Date of Patent: Nov. 20, 2001

(54) J-SHAPED CORONARY SINUS LEAD

(75) Inventors: Mary M. Morris, Mounds View; Xiaoyi Min, Plymouth, both of MN (US)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/264,609

(22) Filed: Mar. 8, 1999

(51) Int. Cl.$^7$ ....................................................... A61N 1/05
(52) U.S. Cl. ............................................ 607/122; 600/374
(58) Field of Search ....................................... 607/122, 123, 607/121; 600/374, 381, 393

(56) References Cited

U.S. PATENT DOCUMENTS

| 4,374,527 |   | 2/1983  | Iversen .          |         |
|-----------|---|---------|--------------------|---------|
| 4,387,717 | * | 6/1983  | Brownlee et al.    | 607/122 |
| 4,402,328 | * | 9/1983  | Doring             | 607/125 |
| 4,414,986 |   | 11/1983 | Dickhudt et al. .  |         |
| 4,506,680 |   | 3/1985  | Stokes .           |         |
| 4,641,656 | * | 2/1987  | Smits              | 607/5   |
| 4,972,848 |   | 11/1990 | DiDomenico et al. .|         |
| 5,282,844 |   | 2/1994  | Stokes et al. .    |         |
| 5,423,772 |   | 6/1995  | Lurie et al. .     |         |
| 5,423,865 |   | 6/1995  | Bowald et al. .    |         |
| 5,433,729 |   | 7/1995  | Adams et al. .     |         |
| 5,445,148 |   | 8/1995  | Jaraczewski et al. .|        |
| 5,476,498 |   | 12/1995 | Ayers .            |         |
| 5,534,022 | * | 7/1996  | Hoffmann et al.    | 607/122 |
| 5,683,445 |   | 11/1997 | Swoyer .           |         |
| 5,871,531 | * | 2/1999  | Struble            | 607/122 |
| 5,885,278 | * | 3/1999  | Fleischman         | 607/122 |
| 5,999,858 | * | 12/1999 | Sommers et al.     | 607/122 |
| 6,064,902 | * | 5/2000  | Haissaguerre et al.| 600/381 |
| 6,212,434 | * | 4/2001  | Scheiner et al.    | 607/123 |

FOREIGN PATENT DOCUMENTS

WO9903530    1/1999  (WO) .............................. A61N/1/05

* cited by examiner

*Primary Examiner*—Kennedy Schaetzle
(74) *Attorney, Agent, or Firm*—Girma Wolde-Michael; Reed Duthler

(57) ABSTRACT

The lead configuration enhances the sensing characteristics of the lead and provides for stable location of the electrodes in the coronary sinus. The J-shaped bend in the distal portion of the lead body spaces the distal tip of the lead body less than about 0.9 inches laterally from the portion of the lead body that is proximal to the bend. The tip of the lead body is provided with a pacing/sensing electrode and the curved portion of the J-shaped bend carries an elongated coil electrode that serves as an indifferent electrode for pacing and sensing. For left atrial pacing, the lead tip electrode is located adjacent the wall of the coronary sinus closest to the left atrium, and the indifferent electrode is located adjacent the opposite wall of the coronary sinus, closer to the left ventricle. To enhance spatial distribution of the indifferent electrode and provide for greater averaging of the ventricular signal, which in turn reduces the far field of the ventricular signal, the indifferent electrode extends over 10–50 millimeters or multiple spaced indifferent electrodes are used.

4 Claims, 4 Drawing Sheets

J-SHAPED CORONARY SINUS LEAD

BACKGROUND OF THE INVENTION

This invention relates generally to implantable electrical leads and more particularly for implantable leads intended for use in the coronary sinus of a patient's heart.

Recently there has been an increased interest in the placement of cardiac pacing and sensing electrodes in the coronary sinus, particularly for purposes of bi-atrial and bi-ventricular pacing. In this context, a number of configurations have been proposed in order to assist in placement and retention of the lead and its electrodes in desired locations within the coronary sinus. Early coronary sinus leads such as the Medtronic Model 6992 Lead had a generally straight lead body configuration and employed a non-conductive tip extending distally from the distal-most electrode as a mechanism for assisting in the insertion of the lead in the coronary sinus and for retaining it in the coronary sinus after insertion. More recently, it has been proposed to provide a body of a coronary sinus lead with a pre-formed sinusoidal or helical configuration in order to allow the lead to expand into contact with the walls of the coronary sinus and thereby retain the lead, much in the same fashion as has been employed in the context of spinal stimulation leads. Coronary sinus leads having such a pre-formed configuration are disclosed in U.S. Pat. No. 5,423,865 issued to Bowald et al. and U.S. Pat. No. 5,476,498 issued to Ayers. Spinal cord stimulation leads having similar pre-formed configurations are disclosed in U.S. Pat. No. 4,374,527 issued to Iversen and U.S. Pat. No. 4,414,986 issued to Dickhudt.

An alternative approach to fabrication of coronary sinus leads has been to provide the distal portion of the lead with a curved configuration corresponding to some extent to the curved configuration of the coronary sinus and great vein. For example, a coronary sinus lead having a continuous multi-radius curvature is disclosed in U.S. Pat. No. 5,433,729 issued to Adams et al. Similar configurations are illustrated in U.S. Pat. No. 5,423,772 issued to Lurie and in U.S. Pat. No. 5,445,148 issued to Jaraczewski. An alternative configuration employing two spaced 45° bends is disclosed in U.S. Pat. No. 5,683,445 issued to Swoyer.

SUMMARY OF THE INVENTION

In the context of coronary sinus leads, it is believed that further improvements in lead configuration can still be made in order to enhance both the sensing characteristics of the coronary sinus lead and to provide for stable location of electrodes in the coronary sinus. The lead of the present invention is intended to accomplish these goals by means of an improved lead body and electrode configuration. In a preferred embodiment, the lead is pre-formed to display a small radius, J-shaped bend in its distal end. In particular, the J-shaped bend is preferably configured such that the distal tip of the lead is spaced less than about 0.9 inches laterally from the portion of the lead proximal to the J-shaped bend. In such a lead, the tip of the lead is provided with a pacing and sensing electrode and the curved portion of the J-shaped distal portion of the lead carries an elongated coil electrode which serves as the indifferent electrode for pacing and sensing. This configuration is optimized to allow placement of the lead in portions of the coronary sinus having a wide variety of diameters.

For example, if the lead is placed in a portion of the coronary sinus having a relatively larger diameter, the lead can be placed such that the distal tip of the lead is curved back more proximally such that the J-shaped curve is compressed to display a reduced radius of curvature, bracing the lead within the coronary sinus and stabilizing the location of the tip electrode. In portions of a coronary sinus having a lesser diameter, the lead may be implanted with the distal tip of the lead directed distally relatively to the lead body such that the J-shaped bend is opened to display a greater radius of curvature, which also braces the lead within the coronary sinus and stabilizes the location of the tip electrode.. In either configuration, the pre-formed J-shaped bend serves to cause the lead to extend across the width of the coronary sinus and to brace the electrode located at the distal end of the lead against the wall of the coronary sinus.

Preferably, for purposes of left atrial pacing, the lead is located so that the tip electrode is located adjacent the wall of the coronary sinus closest to the left atrium. Given the configuration of the lead this necessarily results in the elongated coil indifferent electrode being located at least in part adjacent the opposite wall of the coronary sinus, closer to the left ventricle. The indifferent electrode in preferred embodiments extends over a length of at least about 10 millimeters, in order to provide a large surface area electrode which in turn provides some averaging of the ventricular signal due to the spatial dispersion of the electrode. In other embodiments, the coil electrode may be extended over a substantially greater distance, for example 20 to 50 millimeters in order to further enhance the spatial distribution of the indifferent electrode and provide for a greater averaging of the ventricular signal, in turn reducing the relatively high far field of the ventricular signal relative to the atrial signal and assisting in accurate discrimination between atrial and ventricular signals sensed by the lead. As an alternative, rather than employing a single longer coil electrode, spatial dispersion may be accomplished by provision of multiple spaced indifferent electrodes proximal to the tip electrode to accomplish averaging of the ventricular signal.

In analyzing the ventricular signal sensed in leads generally corresponding to those according to the present invention, the inventors have determined that the ventricular signals sensed at the ends of the indifferent electrodes generally display the highest slew rate, and that this slew rate can be reduced if the end of the indifferent electrode is curved such that it extends generally perpendicular to the axis of the coronary sinus, directed generally away from the ventricle. In order to accomplish this result, in some embodiments, the lead may be configured to employ a longer electrode, for example, 20 millimeters or more in length, and the lead body may be preformed so that as implanted, both ends of the indifferent electrode are curved away from the coronary sinus wall closer to the ventricle and toward the coronary sinus wall adjacent the atrium when the lead is implanted. This may be accomplished by providing a second, preformed bend proximal to the J-shaped bend at the distal end of the lead and directed in an opposite direction or it may be accomplished by other mechanisms, for example, by manufacturing the lead such that the curved portion of the lead carrying the elongated coil electrode is of greater rigidity than the portion of the lead immediately proximal thereto which in turn will encourage the lead to display a similar configuration as implanted.

An additional mechanism for reducing the slew rate of the ventricular signals sensed at the ends of the indifferent electrode is to provide a conductivity reducing coating on one or both end portions of the indifferent electrode. This mechanism may be employed as a substitute or in addition to provision of a spatially dispersed indifferent electrode and/or configuring the indifferent electrode so that the ends of the electrodes are directed away from the ventricles.

DETAILED DESCRIPTION OF THE PREFERRED EMBODIMENTS

Figure 1:
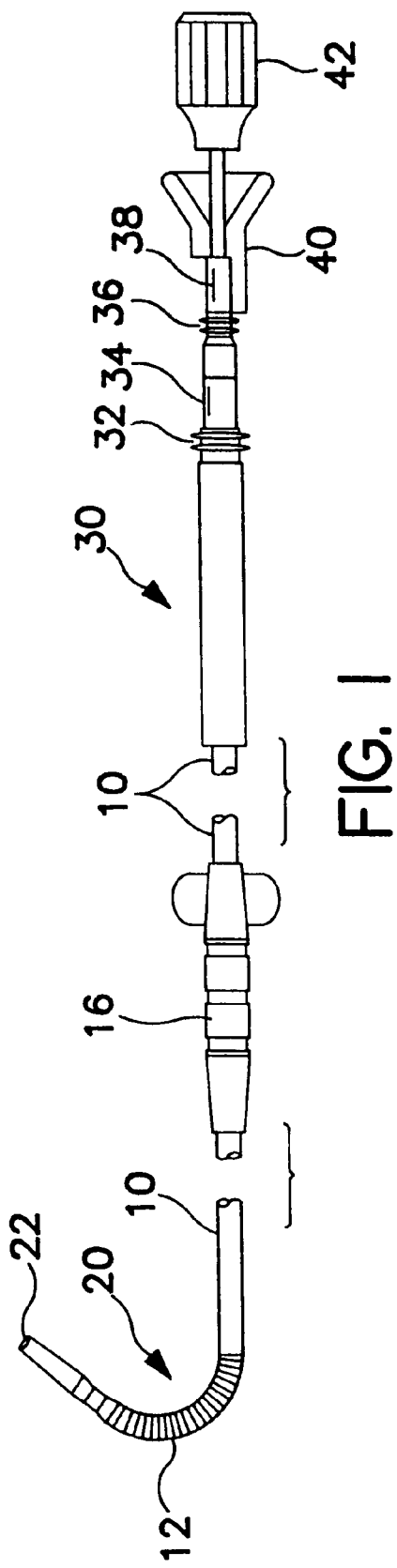
FIG. 1 is a plan view of a first embodiment of a lead according to the present invention.

FIG. 1 is a plan view of a first embodiment of an electrical lead according to the present invention. The lead is provided with an elongated outer insulative sheath 10 which encases two concentrically located, mutually insulated coiled conductors. At the proximal end is located an in-line bipolar connector assembly 30. Connector assembly 30 may correspond to the IS-1 connector standard and is provided with a connector ring 34, a connector pin 38 and two sets of sealing rings 32 and 36 which serve to seal the connector assembly within the bore of an associated implanted pacemaker and to prevent fluid leakage between the connector ring 34 and the connector pin 38. The distal portion 20 of the lead has a generally J-shaped configuration, and includes a pacing/sensing electrode 22 located at the distal tip of the lead and an elongated indifferent electrode 12, extending around the curved portion of the J-shaped distal portion 20 of the lead. Electrode 12 in the illustrated embodiment takes the form of a continuation of one of the two coiled conductors within the outer insulative sheath 10, and extends proximally within the lead to connector assembly 30, where it is coupled to connector ring 34. The second coiled conductor within the lead body is located concentrically within and insulated from coiled conductor 12, and extends from the tip electrode 22 to the connector assembly 30 where it is coupled to connector pin 38. Also illustrated is a stylet 42 inserted through stylet guide 40 into connector pin 38 which stylet may be employed to straighten the lead or to adjust the curvature of the distal portion of the lead to facilitate its installation in the coronary sinus. An anchoring sleeve 16 is also illustrated mounted around the sheath 10.

Figure 2:
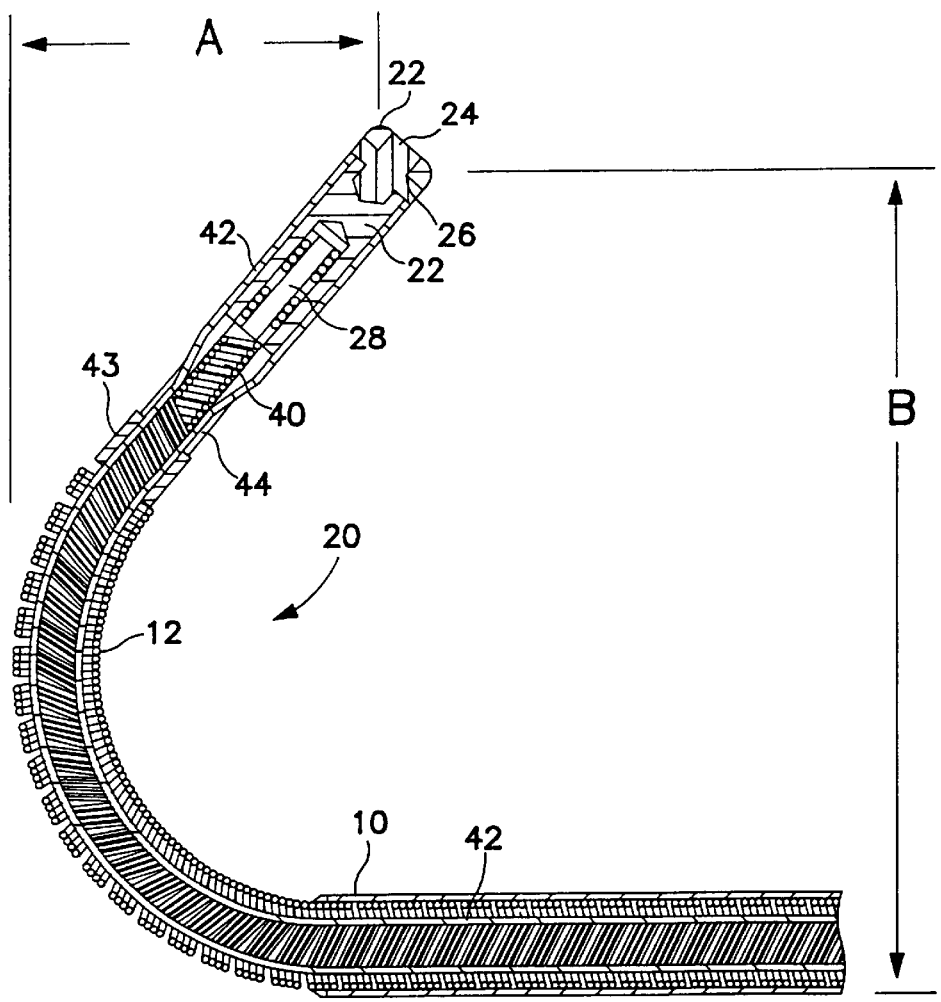
FIG. 2 is a cross-sectional view of the distal portion of the lead of FIG. 1.

FIG. 2 is a cross-sectional view through the J-shaped distal portion 20 of the lead of FIG. 1. In this view, it can be seen that the outer sheath 10 encases conductor 12, the exposed portion of which serves as the indifferent electrode, which in turn encases inner insulative sheath 42, which insulates inner coiled conductor 40 from the outer conductor/indifferent electrode 12. In order to maintain the lead in the J-shaped configuration illustrated, one or more of inner conductor 42, outer conductor/indifferent electrode 12, inner insulative sheath 42 and outer insulative sheath 10 may be pre-formed to display the desired configuration. Conductors 12 and 40 may be any of the numerous conductor types known for use in conjunction with cardiac pacing leads, and in particular may be platinum or tantalum coated MP35N alloy wire. Outer and inner insulative sheaths 10 and 42 may be fabricated of biocompatible plastic such as polyurethane or silicone rubber. As visible in cross-section, tip electrode 22 is provided with a distal-facing bore in which monolithic controlled release device 24 is located. Monolithic controlled release device 24 may correspond to any of the various types of monolithic controlled release devices known to the art including those described in U.S. Pat. No. 5,282,844 issued to Stokes et al., U.S. Pat. No. 4,972,848 issued to DiDomenico et al. and U.S. Pat. No. 4,506,680 issued to Stokes, all incorporated herein in their entireties and preferably elutes an anti-inflammatory steroid such as sodium dexamethasone phosphate or the like in order to reduce irritation of tissue adjacent the electrode. Electrode 22 is also provided with a proximally facing bore in which the distal end of inner conductor 40 is located, along with a crimping core 28. Conductor 40 is coupled to electrode 22 by means of crimps (not illustrated) compressing the lead between electrode 22 and the crimping core 28. Also visible are two plastic bands 43 and 44 which may also be fabricated of polyurethane or silicone rubber and which encircle the inner insulative sleeve 42 distal to the distal end of conductor/electrode 12.

As illustrated, the preferred configuration for this particular embodiment of the lead according to the present invention is a J-shaped bend extending over an arc of approximately 90 to 150 degrees, preferably about 130 degrees. The lead is most preferably configured such that the exposed portion of tip electrode 22 is displaced a distance "B" laterally from the lead body proximal to the curved portion of the J-shaped bend and extends a distance "A" proximally from the distal most portion of the J-shaped bend. In such embodiments the distance "A" may be, for example between about 0.25 and 0.5 inches, while distance "B" may be, for example, between about 0.6 and about 0.9 inches. In the particular embodiment illustrated, configuring the J-shaped distal bend in this fashion facilitates its use in the coronary sinus as illustrated in more detail in FIG. 3 and FIG. 4 below.

Figure 3:
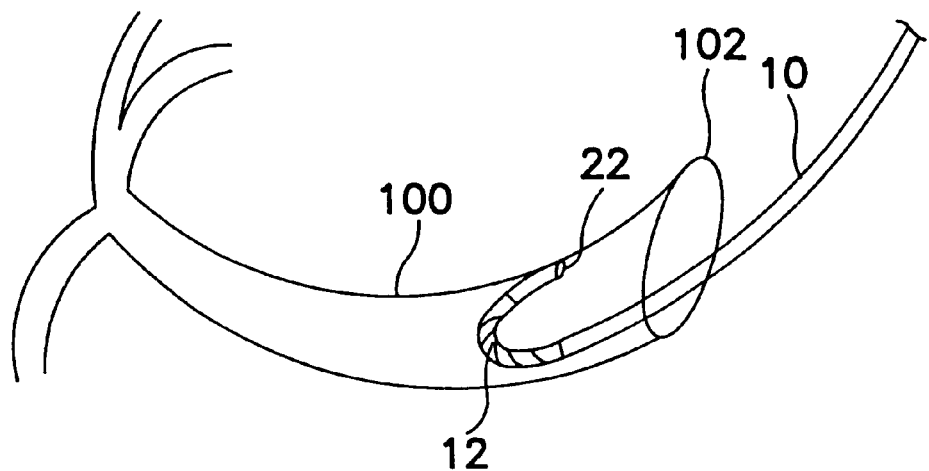
FIGS. 3 and 4 illustrate alternative implantation methods for use in conjunction with the lead of FIG. 1, allowing it to be adapted to portions of a coronary sinus having different diameters.

FIG. 3 illustrates schematically the coronary sinus 100 of a patient's heart, as viewed looking at the posterior surface of the heart. The lead is illustrated entering the ostium 102 of the coronary sinus and is located in this figure in a portion of the coronary sinus that has a relatively larger interior diameter. In this case, the lead is implanted in such a fashion that the distal tip of the lead is directed back proximally, with the tip electrode 22 located adjacent a wall of the coronary sinus 100 closest to the left atrium. In this configuration, the J-shaped bend is somewhat compressed, and the resilience of the lead body tends to cause the lead to expand against the walls of the coronary sinus to brace the lead, maintaining electrode 22 in its desired position. In this view, the elongated indifferent electrode 12 is located such that its proximal end lies generally along the wall of the coronary sinus 102 closer to the ventricle and its distal end is curved and directed away from the wall of the coronary sinus closer to the ventricle.

Figure 4:
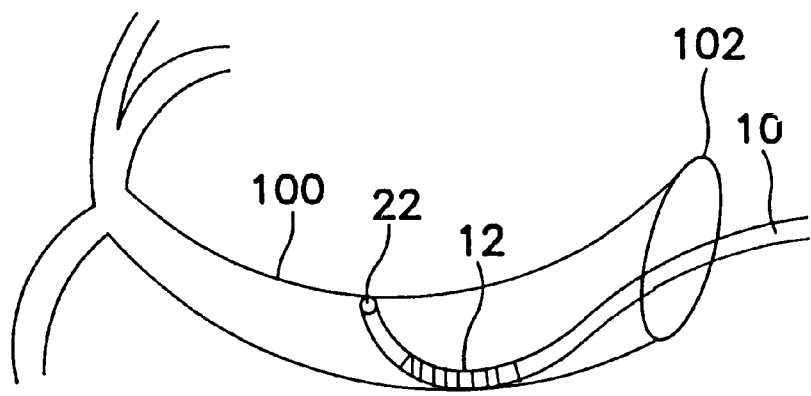

FIG. 4 illustrates the lead of FIG. 1 as implanted in a more distal portion of the coronary sinus 100 of the patient's heart. The lead is shown entering the ostium 102 the coronary sinus, but in this case is located with the distal tip of the lead extending distally, rather than proximally, with the J-shaped bend in this case being opened, rather than compressed. This configuration allows the lead to be implanted in portions of the coronary sinus having a relatively smaller diameter. The resiliency of the J-shaped bend in this case also tends to brace the lead within the coronary sinus and maintain electrode 22 in its desired location. It should be noted that in this configuration, like the configuration illustrated in FIG. 3, the proximal end of electrode 12 lies alongside the wall of the coronary sinus closer to the ventricle while the distal end of electrode 12 is directed away from the wall of the coronary sinus closer the ventricle and toward the wall of the coronary sinus adjacent the atrium.

Implanting the lead as illustrated in FIG. 3 and FIG. 4 is accomplished by inserting a stylet into the lead and advancing the lead to the ostium of the coronary sinus. In order to accomplish the implant configuration illustrated in FIG. 3, the stylet is withdrawn to a point slightly proximal to the beginning of the curved portion of the J-shaped distal end 20 of the lead, and the lead is advanced into the coronary sinus with the curved portion of the J-shaped bend being the most distally located portion of the lead. The implantation configuration of FIG. 4 is accomplished in a similar fashion, with the exception that the stylet is advanced to a point adjacent the tip electrode 22 of the lead and the lead is advanced into the coronary sinus with the tip electrode 22 being the distal-most portion of the lead. The stylet may then be withdrawn to allow the curvature of the distal end to display itself to the degree allowed by the coronary sinus, bracing the tip electrode in its desired location.

While all of the embodiments illustrated in the Figures include an indifferent electrode it should be understood that the configuration of the J-shaped curve as illustrated in FIGS. 1–4 is also valuable in the context of a unipolar pacing lead having only a tip electrode. Similarly, the J-shaped configuration illustrated is also believed valuable in the context of leads having additional electrodes and/or physiologic sensors. In alternative embodiments, the exposed coil electrode may serve as a defibrillation electrode in addition or as an alternative to serving as an indifferent electrode.

Figure 5:
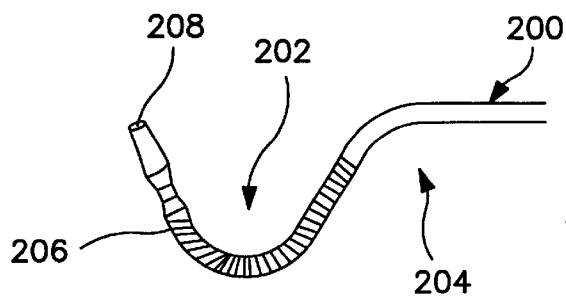
FIG. 5 illustrates the distal portion of an alternative embodiment of a lead according to the present invention, employing an elongated indifferent electrode configured such that the ends of the electrode are directed away from the wall of the coronary sinus adjacent the ventricles, as implanted.
Figure 6:
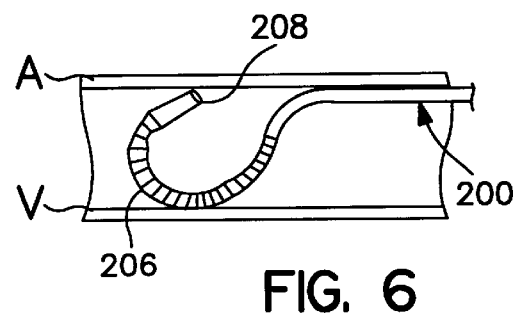
FIGS. 6 and 7 illustrate alternate implantation techniques for the lead of FIG. 7 allowing the lead to be accommodated to portions of the coronary sinus having different internal diameters.
Figure 7:
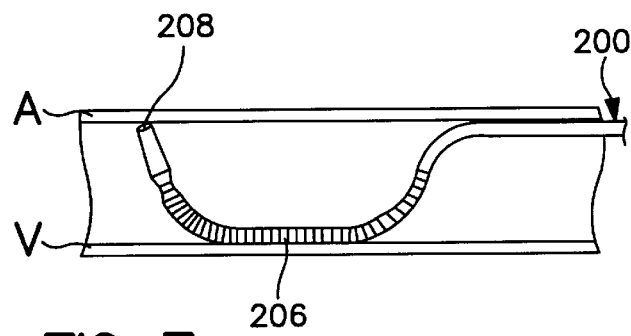

FIG. 5 illustrates an alternative embodiment of a lead according to the present invention, employing an electrode configured such that both the proximal and distal ends of the indifferent electrode are intended to be directed away from the wall of the coronary sinus closer to the ventricle and toward the wall of the coronary sinus adjacent the atrium as implanted, in order to reduce the slew rate of the ventricular signal sensed by the indifferent electrode. In this case, the lead 200 is formed with its distal end including a J-shaped bend 202 which may correspond in configuration to the J-shaped bend of the lead of FIG. 1. Proximal to the J-shaped bend 202 is a second, oppositely directed curved portion 204 which may be pre-formed into the lead body by means of a curvature pre-formed in any of the conductors and/or insulators of the lead body. Alternatively, the lead may be configured to display a curved configuration proximal to the J-shaped bend 202 by the expedient of a flexibility transition, such that the body of the lead 200 is more flexible proximal to the J-shaped bend 202, which again will encourage the lead to display the configuration illustrated from the wall of the coronary sinus adjacent the ventricles and toward the wall A of the coronary sinus most closely adjacent the atrium.

Figure 8:
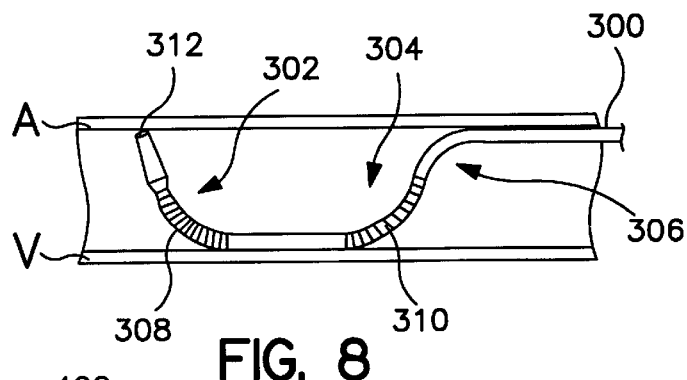
FIG. 8 illustrates an alternate embodiment of the lead in which spatial dispersion of the electrode is accomplished by provision of multiple indifferent electrodes spaced along the lead body.

FIG. 8 illustrates an alternative embodiment in which the indifferent electrodes are dispersed along the lead body in order to accomplish averaging of the ventricular signal. Preferably the electrodes are dispersed over a distance of at least about 20 mm along the lead proximal to the tip electrode. The lead 300 may be provided with a curved configuration including a first J-shaped bend 302 which may correspond to the configuration of the J-shaped bends of the leads of FIGS. 1 and 5. Proximal to the J-shaped bend 302 is a second curved portion 304, and proximal to the second curved portion 304 is a third oppositely directed curved portion 306 winch may correspond to the pre-formed curved portion 304 of the lead in FIG. 5. Alternatively, the lead may be constructed so that the flexibility of the lead proximal to the second curved portion 304 is substantially reduced, in order that the lead will display the curvature illustrated when implanted in the patient's coronary sinus. Located along the curved portion of the J-shaped bend 302 and along the second curved portion 304, tip electrode 312 is shown located adjacent the wall of the coronary sinus adjacent the atrium while electrodes 308 and 310 are shown located in contact with the wall closer to the ventricle and have their distal and proximal ends, respectively, curved and directed away from the wall closer to the ventricle. As illustrated, the lead is configured as it would appear if implanted in a relatively smaller diameter portion of the coronary sinus, with the tip of the lead directed generally distally. However, as discussed in conjunction with the leads of FIGS. 1 and 5, in larger diameter portions of the coronary sinus, the lead may be implanted such that the tip of the lead is directed proximally.

Figure 9:
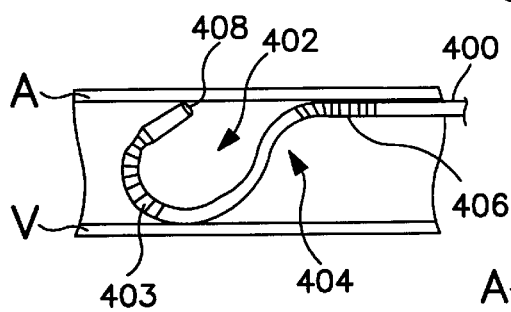
FIG. 9 illustrates yet another alternative embodiment of the present invention in which spatial dispersion of the indifferent electrode is accomplished by means of multiple electrodes located along the lead body.

FIG. 9 illustrates yet another alternative embodiment of the lead according to the present invention accomplishing dispersion of the indifferent electrode by means of the provision of multiple indifferent electrodes spaced from one another along the lead body. The lead 400 is provided with a curved configuration including a J-shaped bend 402 which may correspond to the J-shaped bends of the leads in FIGS. 1 and 5 and a second oppositely directed bend 404 which may correspond to the oppositely directed bends 204 and 306 of the lead in FIGS. 5 and 8. In this case, the indifferent electrode takes the form of two coiled electrodes including a relatively shorter coiled electrode 403 and a second coiled electrode 406 located proximal to the curved portion 404 of the lead body. As implanted, tip electrode 408 is shown located adjacent the wall A of the coronary sinus most closely to the atria. As illustrated, the tip of the lead 400 is directed proximally as would be expected in the context of a lead implanted in a larger diameter portion of the coronary sinus. However, the distal tip of the lead could also be directed distally as discussed above in conjunction with implantation of a lead in smaller diameter portions of the coronary sinus.

Figure 10:
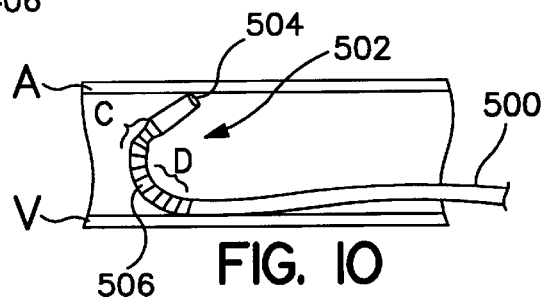
FIG. 10 illustrates an additional alternative embodiment of the present invention in which one or more ends of the indifferent electrode are provided with a conductivity reducing coating in order to reduce the slew rate of ventricular signals sensed at one or both ends of the electrode.

FIG. 10 illustrates yet another embodiment of a lead according to the present invention employing an alternative mechanism to minimize the contribution of the ventricular signal. In this case, the lead 500 has a physical configuration generally identical to that of the lead illustrated in FIG. 1, with a single J-shaped bend 502 extending over the distal portion of the lead. The lead is shown implanted with the tip electrode 504 adjacent the wall of the coronary sinus most adjacent the atrium. In this case, the elongated coiled indifferent electrode 506 is provided with a coating of a voltage attenuating material such as tantalum or tantalum oxide extending over a length "D" of the electrode 506 adjacent the proximal end of the electrode and optionally over a length "C" of the electrode 506 adjacent its distal end. Provision of the voltage attenuating coating reduces slew rates associated with ventricular signals sensed by the distal portions of the leads, and to provide a result similar to that provided by configuring the lead so that the proximal and distal portions of the indifferent electrodes are configured so that they curve away from the wall of the coronary sinus closer to the ventricles and toward the wall of the coronary sinus adjacent the atrium. Such a coating may also be applied to one or both end portions of any of the electrodes illustrated in FIGS. 1–9, in order to enhance the benefits provided by the specific electrode configurations employed by the leads.

In conjunction with the above disclosure, we claim:

1. A cardiac pacing lead for implant in a patient's coronary sinus, comprising:
    an elongated lead body having an outer insulative layer extending over a proximal section and including an elongated conductor therein extending from a proximal end to a distal end; and
    a tip electrode carried on the distal end of the lead body and coupled to the conductor; and
    a portion of the lead body proximal to the tip electrode and distal to the outer insulative layer being configured as a curved, J-shaped segment having a curvature of 90 to 150 degrees, the tip electrode being spaced laterally from the proximal, insulative layer section no more than about 0.9 inches.

2. A lead according to claim 1 wherein the lead further comprises an elongated indifferent electrode extending along the curved segment of the J-shaped portion and having a length of at least about 10 mm and wherein the lead body includes a second conductor coupled to the indifferent electrode.

3. A cardiac pacing lead for implant in a patient's coronary sinus of a patient's heart, comprising:
    an elongated lead body having an outer insulative layer extending over a proximal section and including a pair of elongated conductors therein extending from a proximal end to a distal end; and
    a tip electrode carried on the distal end of the lead body and coupled to one of the conductors; and
    an elongated indifferent electrode carried on the lead body proximal to the tip electrode and distal to the proximal section having the outer insulative layer, the indifferent electrode being coupled to the other of the conductors;
    a portion of the lead body proximal to the tip electrode and distal to the outer insulative layer being configured as a curved, J-shaped segment, the curved portion having a radius of curvature such that, when the tip electrode is positioned during implant adjacent a wall of the coronary sinus closest to the left atrium, the tip electrode extends proximally and the proximal end of the indifferent electrode lies generally along the wall of the coronary sinus closer to the ventricle and curves away from the wall of the coronary sinus to extend generally perpendicular to it.

4. A cardiac pacing lead for implant in a patient's coronary sinus of a patient's heart, comprising:
    an elongated lead body having an outer insulative layer extending over a proximal section and including a pair of elongated conductors therein extending from a proximal end to a distal end; and
    a tip electrode carried on the distal end of the lead body and coupled to one of the conductors; and
    an elongated indifferent electrode carried on the lead body proximal to the tip electrode and distal to the proximal section having the outer insulative layer, the indifferent electrode being coupled to the other of the conductors;
    a portion of the lead body proximal to the tip electrode and distal to the outer insulative layer being configured as a curved, J-shaped segment, the curved portion having a radius of curvature such that, when the tip electrode is positioned during implant adjacent a wall of the coronary sinus closest to the left atrium, the tip electrode extends distally and the proximal end of the indifferent electrode lies generally along the wall of the coronary sinus closer to the ventricle and curves away from the wall of the coronary sinus to extend toward the wall of the coronary sinus adjacent the atrium.

* * * * *